United States Patent
Duplan et al.

(10) Patent No.: US 9,616,010 B2
(45) Date of Patent: Apr. 11, 2017

(54) COSMETIC COMPOSITION COMPRISING A TERNARY LIPID ASSOCIATION FOR CONTROLLING DRYNESS OF THE SKIN

(71) Applicants: PIERRE FABRE DERMO-COSMETIQUE, Boulogne-Billancourt (FR); UNIVERSITE PARIS-SUD 11, Orsay (FR); CENTRE HOSPITALIER UNIVERSITAIRE DE TOULOUSE, Toulouse (FR)

(72) Inventors: Hélène Duplan, Auzeville Tolosan (FR); Daniel Redoules, Toulouse (FR); Alexandre Delalleau, Colomiers (FR)

(73) Assignees: PIERRE FABRE DERMO-COSMETIQUE, Boulogne-Billancourt (FR); UNIVERSITE PARIS-SUD 11, Orsay (FR); CENTRE HOSPITALIER UNIVERSITAIRE DE TOULOUSE, Toulouse (FR)

( * ) Notice: Subject to any disclaimer, the term of this patent is extended or adjusted under 35 U.S.C. 154(b) by 0 days.

(21) Appl. No.: 14/904,286

(22) PCT Filed: Jul. 11, 2014

(86) PCT No.: PCT/EP2014/064972
§ 371 (c)(1),
(2) Date: Jan. 11, 2016

(87) PCT Pub. No.: WO2015/004279
PCT Pub. Date: Jan. 15, 2015

(65) Prior Publication Data
US 2016/0166490 A1    Jun. 16, 2016

(30) Foreign Application Priority Data
Jul. 12, 2013 (FR) ..................... 13 56892

(51) Int. Cl.
| | | |
|---|---|---|
| *A61K 31/56* | (2006.01) | |
| *A61K 8/63* | (2006.01) | |
| *A61K 8/37* | (2006.01) | |
| *A61Q 19/00* | (2006.01) | |
| *A61K 8/06* | (2006.01) | |
| *A61K 8/86* | (2006.01) | |
| *A61Q 1/00* | (2006.01) | |

(52) U.S. Cl.
CPC ............... *A61K 8/63* (2013.01); *A61K 8/06* (2013.01); *A61K 8/37* (2013.01); *A61K 8/375* (2013.01); *A61K 8/86* (2013.01); *A61Q 1/00* (2013.01); *A61Q 19/007* (2013.01); *A61K 2800/592* (2013.01); *A61K 2800/5922* (2013.01)

(58) Field of Classification Search
CPC . A61K 31/56; A61K 8/63; A61K 8/06; A61K 8/37; A61K 8/375; A61K 8/86; A61K 2800/592; A61K 2800/5922; A61Q 1/00; A61Q 19/007
See application file for complete search history.

(56) References Cited

U.S. PATENT DOCUMENTS

| | | |
|---|---|---|
| 3,957,971 A | 5/1976 | Oleniacz |
| 4,604,281 A | 8/1986 | Deckner et al. |
| 2009/0017147 A1 | 1/2009 | Lintner et al. |

FOREIGN PATENT DOCUMENTS

| | | |
|---|---|---|
| EP | 2 583 667 A1 | 4/2013 |
| FR | 2 799 122 A1 | 4/2001 |
| FR | 2 880 802 A1 | 7/2006 |

OTHER PUBLICATIONS

Philippe et al (FR2799122A1, published Apr. 6, 2001, Machine Translation used).*
International Search Report, issued in PCT/EP2014/064972, dated Sep. 24, 2014.
Written Opinion of the International Searching Authority, issued in PCT/EP2014/064972, dated Sep. 24, 2014.
Caussin et al., "FTIR Studies Show Lipophilic Moisturizers to Interact with Stratum Corneum Lipids, Rendering the More Densely Packed," Biochimica et Biophysica Acta, 2008 (Available online Mar. 18, 2008), vol. 1778, pp. 1517-1524.
French Preliminary Search Report, dated Mar. 12, 2014, for corresponding French Application No. 1356892.
International Search Report (Form PCT/ISA/210), dated Sep. 24, 2014, for corresponding International Application No. PCT/EP2014/064972.
Levi et al., "Application of Substrate Curvature Method to Differentiate Drying Stresses in Topical Coatings and Human Stratum Corneum," International Journal of Cosmetic Science, 2010, vol. 32, pp. 294-298.
Levi et al., "Drying Stress and Damage Processes in Human Stratum Corneum," International Journal of Cosmetic Science, 2010, vol. 32, pp. 276-293.
Saad et al., "Infrared Spectroscopic Studies of Sodium Dodecyl Sulphate Permeation and Interaction with Stratum Corneum Lipids in Skin," International Journal of Cosmetic Science, 2012, vol. 34, pp. 36-43.

* cited by examiner

*Primary Examiner* — Jason Sims
*Assistant Examiner* — Brahim Bori
(74) *Attorney, Agent, or Firm* — Birch, Stewart, Kolasch & Birch, LLP

(57) ABSTRACT

The invention relates to a ternary lipid association of β-sitosterol, isocetyl stearoyl stearate and glyceryl tri-2-ethylhexanoate, wherein the β-sitosterol content of said association is between 0.1% and 5 wt. %.

12 Claims, 2 Drawing Sheets

COSMETIC COMPOSITION COMPRISING A TERNARY LIPID ASSOCIATION FOR CONTROLLING DRYNESS OF THE SKIN

The field of the present invention concerns the following novel ternary lipid association: beta-sitosterol, isocetyl stearoyl stearate and glyceryl tri-2-ethylhexanoate; and applications thereof in the fields of cosmetics and dermatology for controlling dryness of the skin.

More particularly, the present invention concerns the cosmetic use of a composition comprising said ternary lipid association, as moisturizing agent for the skin.

Another object of the present invention further concerns a dermatological composition comprising said ternary lipid association for use in the treatment of pathological dry skin.

The skin constitutes an interface between the body and the external environment and as such it not only prevents the penetration of chemical and microbial elements but it must also maintain the body's physiological fluids by limiting water loss. On the latter point, the uppermost layer of the skin, the stratum corneum (referred to as SC throughout the present patent application), makes a substantial contribution to osmotic homeostasis, the role of which is to maintain a water gradient and thus to reduce the drying effects due to the environment. Under physiological conditions, the water content in the superficial part of the skin varies from 70% to 30% while passing from the last living layers (stratum granulosum) to the stratum corneum. It drops further in the very last corneocyte layers to reach 15%.

This ability to maintain water balance comes directly from the structure of the stratum corneum, which consists of flattened keratinized cells—corneocytes—stacked in a lipid matrix. The latter—consisting of ceramides, cholesterol and fatty acids—forms a successive stack of lamellar phases oriented in parallel with the surface of the skin. X-ray diffraction reveals that the lipid chains are organized in two phases: one crystalline, in an orthorhombic arrangement; the other more fluid and less compact, in a hexagonal arrangement. The much more compact crystalline phase predominates in the stratum corneum but the proportion of lipids with hexagonal ordering increases while going toward the surface.

Thus, the integrity of these lipid structures—which provide water-tightness by their hydrophobic nature—is essential to the ability of the stratum corneum to retain water.

The factors tending to promote the drying of the stratum corneum include in particular the use of surfactants (e.g., sodium lauryl sulfate (SLS)) and low environmental humidity (dry cold, heating, etc.). Indeed, it has been shown that the application of SLS reduced the proportion of lipids in an orthorhombic phase and increased that in a hexagonal phase (Saad P, Flach C R, Walters R M, Mendelsohn R. Infrared spectroscopic studies of sodium dodecyl sulfate permeation and interaction with stratum corneum lipids in skin. Int J Cosmet Sci. 2012; 34; 36-43). This damage to the lamellar structures leads to an increase in insensible transepidermal water loss. Similarly, the drying produced by the extended exposure to a low-humidity atmosphere causes the formation of crystalline regions from around which water easily escapes. In these various contexts, the water volume in the uppermost layers decreases and the stratum corneum tends to shrink. Its mechanical properties (tension, elastic modulus) are modified (Levi K, Weber R J, Do J Q, Dauskardt R H. Drying stress and damage processes in human stratum corneum. Int J Cosmet Sci. 2010; 32: 276-93). The skin, having become hard and rough, produces a sensation of discomfort and tightness. At a more severe stage, the stratum corneum loses its barrier quality, which triggers the following responses in particular: increased intraepidermal transpiration, excessive keratinocyte proliferation, modification of the supramolecular arrangement of the lipid matrix. Clinically, the skin becomes thicker and squamous and thus prone to cracking.

When caring for a patient with dry skin, the primary objectives are to improve the patient's skin comfort and quality of life and to restore the stratum corneum to a normal homeostatic state.

Generally, formulators use certain fats that stabilize the lamellar lipid structures of the stratum corneum by limiting the lateral movements of intercorneocyte lipids.

Another alternative for buffering the viscosity of the lipid layers consists in using sterols, which have the property of limiting, as a function of the surrounding drying conditions: the displacement of too-fluid fatty chains or the bringing together of too-rigid fatty chains.

An example of a traditionally used fat is petroleum jelly, the C-26 long chains of which come to be interdigitated with the ceramide bilayers of the stratum corneum. This quasi-occlusive action causes a decrease in water evaporation through the stratum corneum. Similar actions can be obtained using symmetrical long-chain esters, which have the advantage of being less occlusive than petroleum jelly and, consequently, more pleasant to use. The best known include myristyl myristate, cetyl palmitate and isostearyl isostearate. For the latter, studies established that it prevents the phase transition in intercorneocyte lipids (orthorhombic to hexagonal) that occurs with increased temperature (Caussin J, Gooris G S, Bouwstra J A. FTIR studies show lipophilic moisturizers to interact with stratum corneum lipids, rendering the more densely packed. Biochim Biophys Acta. 2008; 1778: 1517-24).

Asymmetrical esters consisting of a long chain and one or more shorter branched chains are still found in many formulas. These esters have the simultaneous advantages of improving the sense of touch provided by the branched chains and acting as a buffer with respect to intercorneocyte lipid spaces. A study carried out on isolated stratum corneum shows the protective effect that certain asymmetrical esters have on the mechanical stresses associated with dehydration stress (Levi et al., Int J Cosmet Sci. 2010; 32: 276-93). Indeed, in this study, the results indicate in particular a good efficacy of isocetyl stearoyl stearate with respect to the shrinking of the stratum corneum specimen desiccated by a lack of moisture. However, it was also observed that derivatives having bulky fatty chains like isocetyl stearoyl stearate could cause an essentially temporary disorganization of intercorneocyte lipid structures before having their stabilizing effect on intercorneocyte lamellar structures. This is seen in particular in FIG. 1, where the topical application of isocetyl stearoyl stearate increases, during the first 4 hours, shrinking of the skin induced by drying stress.

Also it seems necessary to have at hand a moisturizing composition that does not have the disadvantages associated with the use of these asymmetrical long-chain esters.

The goal of the present invention is to provide a novel contribution to dry skin treatments.

During their research, the Inventors demonstrated that by adding to ester isocetyl stearoyl stearate an amount of β-sitosterol less than or equal to 5% by weight relative to the ester, protection against dehydration is distinctly improved.

It was indeed shown that in the biomechanical approach to the SC, consisting in the evaluation of the stress state of dehydrated isolated SC, the association of isocetyl stearoyl stearate with β-sitosterol improves the three criteria selected (see FIG. 2), namely decreasing the maximum stress, the minimum stress and the hydration time.

In a surprising and unexpected manner, it was observed during the biomechanical study of the SC that the addition of a third cosmetic fat, tri-2-ethylhexanoate, to ester isocetyl stearoyl stearate and to β-sitosterol is accompanied by a decrease in, first, the time necessary to reach equilibrium and, second, the stress established at the end of this time.

Thus, the branching on these short-chain triglycerides is essential for the association of the three fats—isocetyl stearoyl stearate, β-sitosterol, and glyceryl tri-2-ethylhexanoate—to enable optimized functioning of the intercorneocyte lipid spaces in a drying environment.

The present invention thus concerns the following ternary lipid association: isocetyl stearoyl stearate, β-sitosterol, and glyceryl tri-2-ethylhexanoate, and more specifically the ternary association wherein β-sitosterol represents from 0.1% to 5% by weight of the association.

According to an additional feature of the present invention, isocetyl stearoyl stearate and glyceryl tri-2-ethylhexanoate are present in said ternary association in substantially equal mass proportions.

Advantageously, the ternary lipid association according to the invention consists of:
5% of β-sitosterol;
47.5% of isocetyl stearoyl stearate, and
47.5% of glyceryl tri-2-ethylhexanoate,
the weight percentages being relative to the total weight of said association.

Another object of the present invention aims at an emollient composition comprising from 1% to 20% of said ternary association; the percentages being expressed by weight relative to the total weight of said composition.

DESCRIPTION OF THE FIGURES

FIG. 1 shows the principle for measuring change in stress after application of an emollient, FIG. 2 shows the three analytical criteria in question: maximum stress, minimum stress and hydration time (action time to reach equilibrium), FIG. 3 shows the results obtained for the following series:
control,
isocetyl stearoyl stearate (ISS)=1,
β-sitosterol+ISS=B1,
β-sitosterol+ISS+glycerol 2-ethylhexanoate=B1T.

Figure 1:
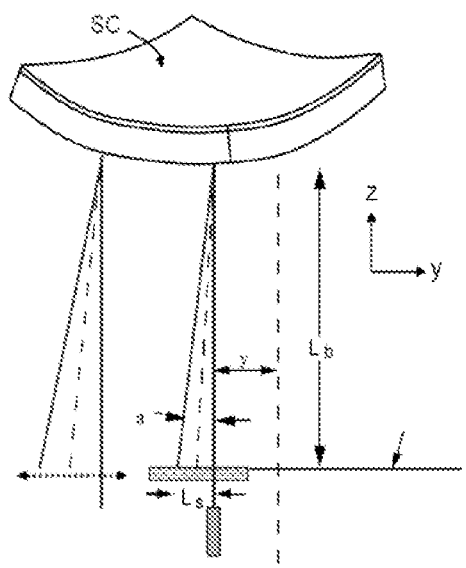
FIGS. 1 to 3 concern the model used to study the stress state of dehydrated isolated SC.
Figure 2:
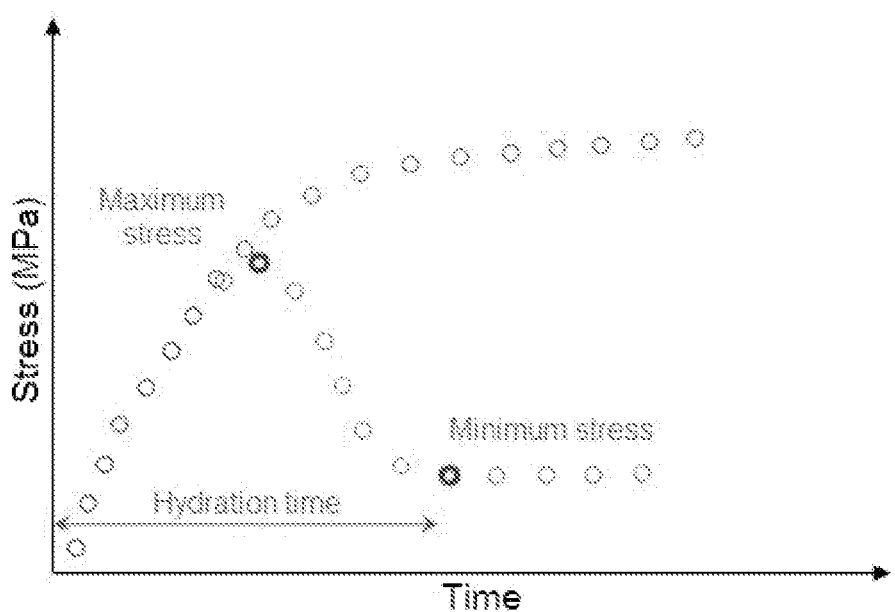

Dehydration of the SC is associated with various mechanisms, such as greater intermolecular forces between intercellular lipids, modification of keratin chains, and a reduction in the water volume of the SC. These phenomena lead to modification of its biophysical properties: thickness, elasticity and tension—which themselves have vital consequences for its integrity.

Relying on macroscopic clinical data on dry skin, and regarding the SC as a surface film and a material, it was suggested that the sensations and appearance of the SC are directly related to its mechanical properties. Thus it is possible to describe and measure sensations of skin discomfort and tension, or the cracked appearance of the SC, by means of biomechanical descriptors of the SC.

These elements led the Applicant to use an in vitro model of isolated SC to study changes in mechanical properties as a function of hydration level. Measuring skin tension makes it possible to define a relationship between skin dryness and skin stress, and the appearance of cracks. Moreover, the use of this model makes it possible to know with a high degree of accuracy the effect of active agents on these mechanical measurements and, consequently, on the hydration state of the stratum corneum. (K. Levi, R. J. Weber, J. Q. Do and R. H. Dauskardt. International Journal of Cosmetic Science, 2010, 32, 276-293 Drying stress and damage processes in human stratum corneum) (K. Levi and R. H. Dauskardt. International Journal of Cosmetic Science, 2010, 32, 294-298 Application of substrate curvature method to differentiate drying stresses in topical coatings and human stratum corneum).

The composition according to the invention enables a decrease in skin stress and tension, and thus a decrease in sensations of tight skin and a decrease in redness, cracks and/or chapping.

In a particular embodiment of the invention, the composition further comprises one or more other humectants to supplement the action of the ternary lipid association.

Generally, all the approaches aimed at strengthening the functional aspect of intercorneocyte lipids under drying conditions are combined in emulsions with hygroscopic humectants such as glycerol, urea, sorbitol, etc.

In another particular embodiment of the invention, the composition further comprises one or more other cosmetic or dermatological active ingredients.

For example, mention may be made of di(guanosine-5') tetraphosphate (GP4G), a marine biotechnology active ingredient extracted from the zooplankton *Artemia salina*, known for its stimulation of mitochondrial activity and cellular metabolism.

Preferably, the compositions according to the invention will be administered topically.

More preferably, the compositions according to the invention take the form of an emulsion.

They could be skincare and/or makeup products for the body and/or face.

Another aspect of the present invention concerns the cosmetic use of the composition according to the invention as a moisturizing agent for the skin.

More particularly, said composition is for moisturizing the epidermis, in particular the stratum corneum. The present invention also aims at a cosmetic method for moisturizing the skin comprising the application on the skin of an emollient composition according to the invention.

Finally, another object of the present invention is to provide a dermatological composition comprising said ternary lipid association for use in the treatment of pathological dry skin.

By "pathological dry skin" is meant, in the context of the present invention, any type of dry skin, either directly related to skin pathology or resulting from the dermatological treatment thereof.

More particularly, said composition is for improving the symptoms of any form of pathological dry skin in terms of appearance, such as roughness or associated perceptions (pruritus, tightness).

EXAMPLES

Moisturizing Care

| INCI name | Percentage | Function |
|---|---|---|
| Purified water | QS 100% | |
| Glycerin | 3 | Humectant |

-continued

| INCI name | Percentage | Function |
|---|---|---|
| Disodium EDTA | 0.1 | Complexing agent |
| Phenoxyethanol | 0.35 | Preservative |
| Polyacrylate-13 & Polyisobutene & Polysorbate 20 & Water | 1 | Gelling agent, stabilizer |
| Glyceryl stearate & PEG-100 stearate | 4 | Emulsifier |
| Cetyl alcohol | 1 | Consistency factor |
| Caprylic/capric triglycerides | 6 | Emollient |
| Paraffinum liquidum | 4 | Emollient |
| Dicaprylyl carbonates | 4 | Emollient |
| Ternary lipid association (B 5% - 1 47.5% - T 47.5%) | 3% | Active agent |
| Fragrance | 0.1 | Fragrance |

Moisturizing Care Serum:

| INCI name | Percentage | Function |
|---|---|---|
| Water | QS 100% | |
| Glycerin | 3 | Humectant |
| Disodium EDTA | 0.1 | Complexing agent |
| Glycol | 0.3 | Humectant |
| Sodium polyacrylate | 1 | Gelling agent, stabilizer |
| Dimethicone | 4 | Emollient |
| Myristyl alcohol & Myristyl glucoside | 2 | Consistency factor |
| Benzoic acid | 0.3 | Preservative |
| Ternary lipid association (B 5% - 1 47.5% - T 47.5%) | 6% | Active agent |
| Fragrance | 0.1 | Fragrance |

Evaluation:

The mechanical approach used here consists in measuring the mechanical stress produced within SC that has been isolated and subjected to dehydration stress in an environmental chamber.

The SC specimen—from human skin explants—was isolated by enzymatic digestion. It was placed on a borosilicate slide to which it naturally adheres.

The SC, initially 100% hydrated, is then placed in an atmosphere with 7% air humidity. The SC then undergoes a progressive dehydration, during which measurements of SC tension are taken every 15 minutes for 8 hours using a stress measurement device. Notably due to lost water volume, the stratum corneum shrinks during dehydration. Given the differences that exist between its mechanical properties and those of the support (the slide), the latter bends. By means of this radius of curvature, measured with a laser interferometer, it is then possible to calculate the state of tension/stress from the Stoney equation. The initial data correspond to a measurement of the variation of the curvature of the unit (borosilicate slide+SC). It is possible to calculate the biomechanical stress parameters of the SC, such as tension, from knowledge of the biomechanical properties of the borosilicate slide, its thickness, and the thickness of the SC (see methodology FIG. 1; and bibliographical reference K. Levi, et al., IJCS 2010).

This first kinetics study makes it possible to know the behavior of untreated SC. Next, the unit (SC+slide) is returned to 100% air humidity for 2 hours and then incubated in the various treatments for 5 minutes. A 50 m film is deposited: using a spiral filmograph for liquid emollients and a slide for creams. At the end of this period the unit is again placed in 7% air humidity for the study of dehydration kinetics until stabilization of the measurements (generally 8 to 12 hours). The kinetics of the development of stress within SC subjected to dehydration stress are studied and compared with the "Water" control, which corresponds to the no-treatment condition.

Descriptions of the Composition of the Mixtures:
1: 100% isocetyl stearoyl stearate (ISS)
B1: β-sitosterol (5%)+ISS (95%)
B1T: β-sitosterol (5%)+ISS (47.5%)+glyceryl tri-2-ethylhexanoate (47.5%)

Figure 3:
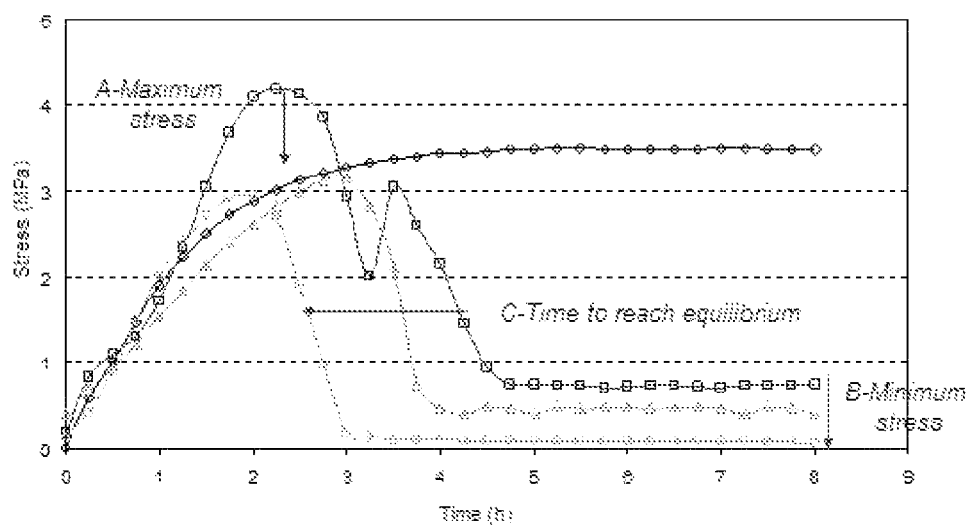

Interpretation of the Curves, Conclusion:

In FIG. 3, the control corresponds to untreated SC before dehydration kinetics (-◇-). Shown are measurements of mechanical stresses within the SC (MPa) as a function of dehydration kinetics (h). These stresses increase with the drop in the air humidity, as a function of time, until reaching a plateau.

When the SC is pretreated with 100% ISS (1--□-), the curve shows a maximum stress that is momentarily greater than the control but that quickly falls (starting after 3 hours of dehydration) to reach a minimum stress plateau after 2 hours.

When the ISS is supplemented with 5% of β-sitosterol (B1--Δ-) and then with 47.5% of glyceryl tri-2-ethylhexanoate, the minimum stress plateau is further decreased and reached more quickly.

The association in trio form is most effective for limiting the generation of mechanical stresses within the SC during drying (B1T--○-).

It was thus shown that this association prevents the shrinking of the stratum corneum under dry conditions while moderating the destabilization of the lipid spaces generated by the ester isocetyl stearoyl stearate. Comparing the curves of FIG. 3, it is quite evident that adding 5% by weight of β-sitosterol to the asymmetrical ester not only avoids excess stress due to the hindrance of the ester but also makes it possible to decrease the latter to a level substantially lower than the equilibrium state. In our experimental model, this equilibrium state is reached after a period of time of 3 to 5 hours depending on the treatment and corresponds in all likelihood to the time needed for the emollient substances to penetrate into the intercorneocyte lipid spaces in order to stabilize the latter.

For reasons of solubility, the proportion of β-sitosterol within said association should not be greater than 5%. This 5% value consequently appears to be the best compromise in terms of product efficacy.

Use of the composition B1T [ISS (47.5%), β-sitosterol (5%), glyceryl tri-2-ethylhexanoate (47.5%)] makes it possible to reach the minimum stress more quickly than a composition B1 or 1 (FIG. 3).

The invention claimed is:

1. Ternary lipid association consisting of β-sitosterol, isocetyl stearoyl stearate and glyceryl tri-2-ethylhexanoate, wherein β-sitosterol is present in a proportion of 0.1% to 5% by weight of said association.

2. Ternary lipid association according to claim 1, characterized in that isocetyl stearoyl stearate and glyceryl tri-2-ethylhexanoate are present in mass proportions.

3. Ternary lipid association according to claim 1, characterized in that it has the following composition:
   5% of β-sitosterol
   47.5% of isocetyl stearoyl stearate, and
   47.5% of glyceryl tri-2-ethylhexanoate the percentages being expressed by weight relative to the total weight of said association.

4. An emollient composition comprising from 1% to 20% of ternary lipid association consisting of β-sitosterol, isocetyl stearoyl stearate and glyceryl tri-2-ethylhexanoate, wherein β-sitosterol is present in a proportion of 0.1% to 5% by weight of said association, the percentages being expressed by weight relative to the total weight of said composition.

5. Composition according to claim 4 characterized in that it further comprises one or more other humectants.

6. Composition according to claim 4 characterized in that it further comprises another cosmetic active agent, and in particular GP4G.

7. Composition according to claim 4 characterized in that it takes the form of an emulsion.

8. Composition according to claim 4, characterized in that it takes the form of a skincare and/or makeup product for the body or face.

9. A method for moisturizing skin, comprising: applying the composition according to claim 4 to the skin.

10. The method according to claim 9, wherein the composition is applied to the stratum corneum.

11. A method for treating pathological dry skin, comprising: applying the composition according to claim 4 to the pathological dry skin.

12. The method according to claim 11, wherein the method treats at least one symptom of pathological dry skin comprising roughness, pruritis, or tightness.

* * * * *